United States Patent
Correnti

(10) Patent No.: US 12,046,373 B2
(45) Date of Patent: *Jul. 23, 2024

(54) AUTOMATED SURFACE STERILIZATION TECHNIQUES

(71) Applicant: Alarm.com Incorporated, Tysons, VA (US)

(72) Inventor: Matthew Daniel Correnti, Newtown Square, PA (US)

(73) Assignee: Alarm.com Incorporated, Tysons, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/863,772

(22) Filed: Jul. 13, 2022

(65) Prior Publication Data
US 2022/0359086 A1 Nov. 10, 2022

Related U.S. Application Data

(63) Continuation of application No. 16/692,705, filed on Nov. 22, 2019, now Pat. No. 11,398,309.

(60) Provisional application No. 62/771,629, filed on Nov. 27, 2018.

(51) Int. Cl.
*G16H 50/30* (2018.01)
*G16H 40/67* (2018.01)

(52) U.S. Cl.
CPC .............. *G16H 50/30* (2018.01); *G16H 40/67* (2018.01)

(58) Field of Classification Search
CPC ................................ G16H 50/30; G16H 40/67
USPC ........................................................ 705/2–3
See application file for complete search history.

(56) References Cited

U.S. PATENT DOCUMENTS

| | | | |
|---|---|---|---|
| 4,595,419 A * | 6/1986 | Patenaude | F22B 37/003 376/310 |
| 6,459,955 B1 | 10/2002 | Bartsch et al. | |
| 8,963,623 B2 * | 2/2015 | Siao | H02M 3/073 327/536 |
| 8,965,623 B2 | 2/2015 | Rakshit | |
| 10,463,217 B1 * | 11/2019 | Bialek | A47L 9/2857 |
| 11,069,070 B2 | 7/2021 | Buibas et al. | |
| 11,416,878 B2 | 8/2022 | Koch et al. | |

(Continued)

OTHER PUBLICATIONS

Cairns, Rebecca, "What temperature kills germs? How to use heat properly to get rid of bacteria and viruses," Insider, Mar. 12, 2020, 14 pages.

(Continued)

*Primary Examiner* — Michael Tomaszewski
(74) *Attorney, Agent, or Firm* — Fish & Richardson P.C.

(57) ABSTRACT

Systems and techniques are described for using a robotic device to autonomously monitor activity within a property to predict a high likelihood of germ or disease transmission, and in response, perform one or more sterilization operations to regions of a property to reduce the likelihood of germ or disease transmission. In some implementations, sensor data collected by one or more sensors located within a property is processed. One or more activity patterns of a user located within the property based on processing the sensor data is identified. A determination to perform a sterilization operation based on the one or more activity patterns of the user is made. An instruction is provided to a robotic device located in the property to perform the sterilization operation.

20 Claims, 8 Drawing Sheets

(56) References Cited

U.S. PATENT DOCUMENTS

| | | | |
|---|---|---|---|
| 11,631,279 B2 | 4/2023 | Madden et al. | |
| 2006/0184293 A1* | 8/2006 | Konandreas | A47L 11/4083 701/23 |
| 2006/0190132 A1* | 8/2006 | Morse | A47L 11/4002 700/245 |
| 2006/0190133 A1* | 8/2006 | Konandreas | A47L 11/4011 700/245 |
| 2006/0190134 A1* | 8/2006 | Ziegler | A47L 11/4041 700/245 |
| 2006/0190146 A1* | 8/2006 | Morse | A47L 11/34 701/25 |
| 2006/0200281 A1* | 9/2006 | Ziegler | A47L 11/4011 701/23 |
| 2007/0231189 A1* | 10/2007 | Jung | A61L 2/10 422/62 |
| 2007/0231193 A1* | 10/2007 | Jung | A61L 2/084 250/455.11 |
| 2007/0231204 A1* | 10/2007 | Hyde | A61L 2/07 422/62 |
| 2010/0111775 A1* | 5/2010 | Hyde | A61L 2/08 422/292 |
| 2010/0256812 A1* | 10/2010 | Tsusaka | B25J 9/0003 700/254 |
| 2011/0002821 A1* | 1/2011 | Hyde | A61L 2/07 422/292 |
| 2011/0167574 A1* | 7/2011 | Stout | G05D 1/0257 701/25 |
| 2012/0213443 A1* | 8/2012 | Shin | G06T 7/246 901/1 |
| 2012/0223216 A1* | 9/2012 | Flaherty | A61L 2/24 901/1 |
| 2013/0270459 A1* | 10/2013 | Fontani | A61L 2/10 901/1 |
| 2014/0207280 A1* | 7/2014 | Duffley | A47L 11/4011 700/257 |
| 2014/0207281 A1* | 7/2014 | Angle | B25J 13/006 700/257 |
| 2014/0207282 A1* | 7/2014 | Angle | H04L 67/62 901/1 |
| 2014/0236351 A1* | 8/2014 | Hyde | G16H 40/67 700/244 |
| 2014/0279458 A1* | 9/2014 | Holman | G06Q 20/102 705/40 |
| 2014/0324271 A1* | 10/2014 | Oh | G05D 1/0274 701/28 |
| 2014/0330452 A1* | 11/2014 | Stewart | B25J 19/02 701/2 |
| 2014/0358573 A1* | 12/2014 | Balinski | G16H 40/20 705/2 |
| 2015/0166060 A1* | 6/2015 | Smith | G01S 15/88 701/23 |
| 2015/0197012 A1* | 7/2015 | Schnittman | G05D 1/0227 700/250 |
| 2015/0250372 A1* | 9/2015 | T P | A47L 11/4011 701/28 |
| 2016/0103451 A1* | 4/2016 | Vicenti | B25J 11/0085 700/259 |
| 2016/0104084 A1 | 4/2016 | Philip et al. | |
| 2016/0274579 A1* | 9/2016 | So | G05D 1/2235 |
| 2017/0080570 A1* | 3/2017 | Schnittman | G05D 1/027 |
| 2017/0197713 A1* | 7/2017 | Borman | A47L 11/4066 |
| 2018/0070787 A1* | 3/2018 | Gordon | A47L 9/2847 |
| 2018/0085927 A1 | 3/2018 | Kapoor et al. | |
| 2018/0125320 A1* | 5/2018 | Peck | A47L 11/4022 |
| 2018/0252534 A1 | 9/2018 | Kuhara et al. | |
| 2018/0296711 A1 | 10/2018 | Brais et al. | |
| 2018/0344116 A1* | 12/2018 | Schriesheim | A47L 9/2857 |
| 2019/0015984 A1* | 1/2019 | Kim | G05D 1/0044 |
| 2019/0102876 A1 | 4/2019 | Sanders et al. | |
| 2019/0117809 A1* | 4/2019 | Katz | G06V 20/52 |
| 2019/0176321 A1 | 6/2019 | Afrouzi et al. | |
| 2019/0191950 A1* | 6/2019 | Luo | A47L 11/283 |
| 2019/0212752 A1* | 7/2019 | Fong | G06V 10/764 |
| 2019/0239709 A1 | 8/2019 | Thomas | |
| 2019/0343355 A1* | 11/2019 | Han | A47L 9/2815 |
| 2020/0100639 A1* | 4/2020 | Ullmann | G05B 19/19 |
| 2020/0268225 A1* | 8/2020 | Ashbaugh | A47L 11/185 |
| 2020/0380701 A1 | 12/2020 | Buibas et al. | |
| 2021/0177226 A1 | 6/2021 | Burns et al. | |
| 2021/0235954 A1* | 8/2021 | Papenheim | G05D 1/0219 |
| 2022/0047141 A1* | 2/2022 | Xu | A47L 11/4055 |
| 2022/0087498 A1 | 3/2022 | Madden et al. | |
| 2022/0092298 A1 | 3/2022 | Madden et al. | |
| 2022/0269943 A1* | 8/2022 | Szatmary | G06N 5/04 |
| 2023/0000302 A1* | 1/2023 | Oyaizu | G06T 7/0008 |
| 2023/0079349 A1* | 3/2023 | Jiang | A47L 9/0477 134/18 |
| 2023/0168670 A1* | 6/2023 | von Reventlow | G05D 1/0231 701/2 |

OTHER PUBLICATIONS

Emont, Jon, "Will Warmer Temperatures Bring a Coronavirus Reprieve? It's Complicated; Many scientists predict reduced spread in warm months, but can't say by how much," Wall Street Journal (online), Apr. 13, 2020, 3 pages.

* cited by examiner

700

OBTAIN A COMMUNICATION RELATED TO A STERILIZATION OPERATION ASSOCIATED WITH A PROPERTY
710

OBTAIN SENSOR DATA COLLECTED BY ONE OR MORE SENSORS LOCATED WITHIN THE PROPERTY
720

IDENTIFY ONE OR MORE SURFACES WITHIN THE PROPERTY FOR THE STERILIZATION OPERATION
730

PERFORM THE STERILIZATION OPERATION
740

800

```
PROCESS SENSOR DATA COLLECTED BY ONE OR MORE SENSORS
LOCATED IN A PROPERTY
                                                    810
```

```
IDENTIFY ONE OR MORE ACTIVITY PATTERNS OF A USER LOCATED WITHIN
THE PROPERTY
                                                    820
```

```
DETERMINE TO PERFORM A STERILIZATION OPERATION
                                                    830
```

```
PROVIDE AN INSTRUCTION TO A ROBOTIC DEVICE LOCATED IN THE
PROPERTY TO PERFORM THE STERILIZATION OPERATION
                                                    840
```

AUTOMATED SURFACE STERILIZATION TECHNIQUES

CROSS-REFERENCE TO RELATED APPLICATIONS

This application is a continuation of U.S. application Ser. No. 16/692,705, filed Nov. 22, 2019, now allowed, which claims the benefit of U.S. Provisional Patent Application No. 62/771,629 filed on Nov. 27, 2018 and titled "AUTOMATED SURFACE STERILIZATION TECHNIQUES." The disclosure of each of the foregoing applications is incorporated herein by reference.

TECHNICAL FIELD

This disclosure relates to home monitoring technology.

BACKGROUND

A monitoring system for a property can include various components including sensors, cameras, and other devices. A user can configure the monitoring system by placing components in certain locations of the property. For instance, placement of components within certain locations can be used to perform maintenance operations.

SUMMARY

Many property monitoring systems often include robotic components with automated cleaning functionalities, for example, robot vacuums, robot lawn mowers, automated appliances, or robot window cleaners. However, while many such property management systems can be used to automate certain cleaning functions, they are not focused on sterilizing surfaces of a property to reduce the transmission of germs or diseases between occupants. For example, while a robot cleaning device might clean individual surfaces of a property, without accessing activity or usage information, the robot cleaning device will be unable to track usage of cleaned surfaces in relation to cleaning. Many property monitoring systems with static or predefined cleaning configurations are therefore unable to properly sterilize properties to reduce the spread of germs by a sick occupant.

Accordingly, techniques are described for using a robotic device, such as a drone, to autonomously monitor activity within a property to predict a high likelihood of germ or disease transmission, and in response, automatically perform one or more sterilization operations to regions of a property to reduce the likelihood of germ or disease transmission. For example, the robotic device can include sensors that are capable of collecting or accessing activity data of users within a property to assess the likelihood that germ or disease transmission related to high-risk surfaces of the property, e.g., door knobs, handles, tables, etc. The robotic device can also include a robotic arm to carry sterilization equipment, such as an ultraviolet (UV) irradiation device, disinfectant sprays, a heat lamp, or a laser ablation device, that enables the robotic device to sterilize surfaces of a property with minimal or no human intervention. In some instances, the robotic device can also include additional on-board sensors to detect biological residues in air circulation or high-risk surfaces.

Implementations of the described techniques may include hardware, a method or process implemented at least partially in hardware, or a computer-readable storage medium encoded with executable instructions that, when executed by a processor, perform operations.

The details of one or more implementations are set forth in the accompanying drawings and the description below. Other features will be apparent from the description and drawings.

DESCRIPTION OF DRAWINGS

In the drawings, like reference numbers represent corresponding parts throughout.

DETAILED DESCRIPTION

Figure 1:
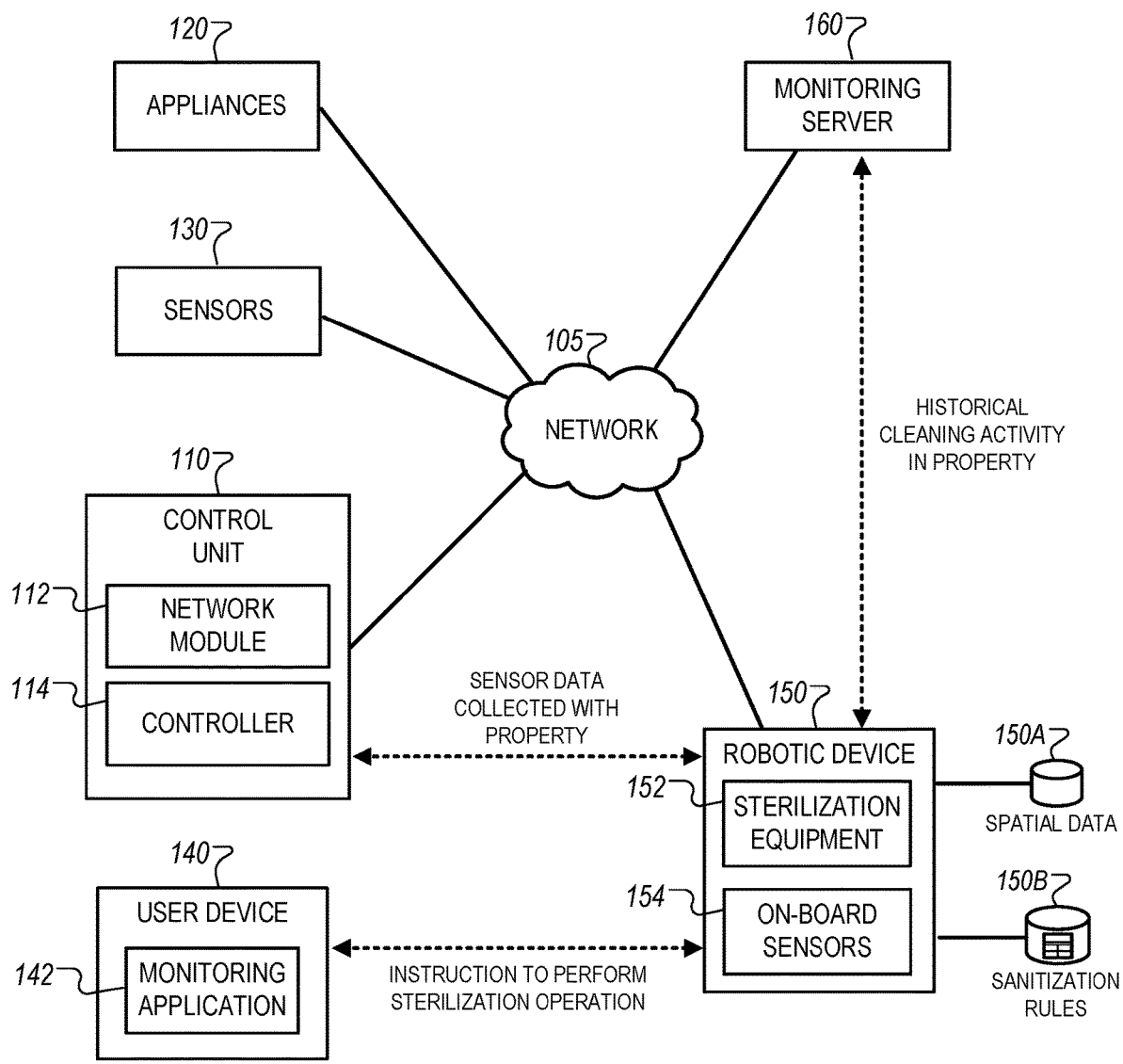
FIG. 1 illustrates an example of a system that is capable of automatically sterilizing surfaces within a property using a robotic device.

In general, techniques are described for using a robotic device, such as a drone, to autonomous monitor activity within a property to predict a high likelihood of germ or disease transmission, and in response, automatically perform one or more sterilization operations to regions of a property to reduce the likelihood of germ or disease transmission. For example, the robotic device can include sensors that are capable of collecting activity data of users within a property to assess the likelihood that germ or disease transmission related to high-risk surfaces of the property, e.g., door knobs, handles, tables, etc. Additionally or alternatively, sensors separate from the robotic device and within a home may be used to collect activity data and that data may be then provided to the robotic device. The robotic device can also include a robotic arm to carry sterilization equipment, such as an ultraviolet (UV) irradiation device, disinfectant sprays, a heat lamp, or a laser ablation device, that enables the robotic device to sterilize surfaces of a property with minimal or no human intervention. In some instances, the robotic device can also include additional on-board sensors to detect biological residues in air circulation or high-risk surfaces.

As described throughout, "sterilization" refers to a process that eliminates, removes, kills, or deactivates forms of life and other biological agents, e.g., fungi, bacteria, viruses, spore forms, priors, etc., present in a specified region, such as a surface, a volume of fluid, among others. In the context of property monitoring, sterilization techniques can be used to, for example, reduce the transmission of diseases between occupants and/or improve the treatment of an occupant that is already inflicted with a disease condition. Sterilization can be achieved through various means, including the application of heat, chemicals, irradiation, high pressure, or filtration. In certain instances, a sterilization operation involves disinfection, sanitization, and pasteurization.

As described throughout, "real-time" refers to information or data that is collected and/or processed instantaneously with minimal delay after the occurrence of a specified event, condition, or trigger. For instance, "real-time data" refers to data, e.g., sensor data, that is processed with minimal delay after a sensor collects or senses the data, e.g., using a light sensing element. The minimal delay in collecting and processing the collected data is based on a sampling rate or monitoring frequency of the sensor, and a time delay associated with processing the collected data and transmitting the processed data to a receiving device, e.g., a robotic device. As an example, on-board sensors of a robotic device collect spatial data in real-time to monitor changes in the interior environment of a property over time and/or compare the collected spatial data to known or expected conditions for the interior environment of the property. The system processes the collected on-board sensor data to determine whether surfaces of the property should be sterilized.

FIG. 1 illustrates an example of a system 100 that is capable of automatically sterilizing surfaces within a property using a robotic device. The system 100 can include a control unit 110, appliances 120, sensors 130, a user device 140, a robotic device 150, and a monitoring server 160 that exchange communications over a network 105. The system 100 can be installed within a property where the control unit 110, the sensors 130, the appliances 120, and the robotic device 150 are located.

In general, the system 100 can be used to reduce the risk of germ or disease transmission within a property by using the robotic device 150 to perform sterilize operations that kill or remove germs from certain high-risk surfaces of a property. In some examples, a user manually instructs the robotic device 150 to perform a sterilization operation through a monitoring application 142 that configures the robotic device 150. In such examples, the user can specify regions of interest for the robotic device 150 to automatically monitor and sterilize with minimal human intervention.

In some other examples, the robotic device 150 can navigate through an interior environment of the property and use collected sensor data, e.g., data collected by the sensors 130 or data collected by on-board sensors 154, to determine a high likelihood of germ or disease transmission within the property. In such examples, the robotic device 150 classifies the type of risk involved, e.g., bacterial infection, biological contamination, etc., and performs the appropriate type of sterilization procedure based on the risk classification with no human intervention. In this respect, in some instances, the robotic device 150 can operate autonomously without a user having to instruct it to perform a sterilization operation, thereby reducing the risk of germ or disease transmission in scenarios where users are unaware of risks.

Referring now to the components of the system 100, the network 105 may be configured to enable electronic communications between electronic devices. For example, the network 105 may be configured to enable exchange of electronic communications between the control unit 110, the appliances 120, the sensors 130, the user device 140, the robotic device 150, and the monitoring server 160.

The network 105 may include Local Area Networks (LANs), Wi-Fi, or analog or digital wired and wireless networks. The network 105 may include multiple networks or subnetworks, each of which may include, for example, a wired or wireless data pathway. The network 105 may also include a circuit-switched network, a packet-switched data network, or any other network able to carry electronic communications (e.g., data or voice communications). For example, the network 105 may include networks based on the Internet protocol (IP), or other comparable technologies. In some examples, the network 105 may include wide area networks (WAN) of computers that receive services provided by a service provider.

The control unit 110 can be a computing device that controls aspects of monitoring operations performed by the components of the system 100. The control unit 110 can include a network module 112 and a controller 114. The network module 112 can be a communication device configured to exchange communications over the network 105. The network module 112 can be a wireless communication module configured to exchange wireless communications over the network 105. For example, the network module 112 can be a wireless communication device configured to exchange communications over a short-range wireless network. The network module 112 can also be configured to exchange communications over the network 105 using a wireless connection. For instance, the network module 112 can enable the control unit 110 to exchange communications with the monitoring server 160 over the network 105 without the use of the network 105. The wireless communication device can include one or more GSM modules, a radio modem, a cellular transmission module, or any type of module configured to exchange communications in one of the following formats: LTE, GSM or GPRS, CDMA, EDGE or EGPRS, EV-DO or EVDO, UMTS, IP, or Wi-Fi.

The network module 112 can also may be a wired communication module configured to exchange communications over the network 105 using a wired connection. For instance, the network module 112 can be a modem, a network interface card, or another type of network interface device. The network module 112 can be an Ethernet network card configured to enable the control unit 110 to communicate over a local area network and/or the Internet. The network module 112 can also be a voiceband modem configured to enable an alarm panel to communicate over the telephone lines of Plain Old Telephone Systems (POTS). In some implementations, the alarm panel may be a broadband or cellular gateway where the network module may enable the control unit 110 to communicate over the network 105.

The controller 114 can be configured to control, for example, the collection of sensor data by the sensors 130 and/or the robotic device 150 or instructing the robotic device 150 to perform a sterilization operation. In these examples, the controller 114 can be configured to receive input from the sensors 130 or other devices associated with the system 100 and control operation of components of the system 100, such as a camera, a temperature sensor, an activity sensor, HVAC components, etc. For example, the controller 114 may be configured to control operation of the network module 112 included in the control unit 110.

The control unit 110 can communicate with the appliances 120, the sensors 130, the user device 140, the robotic device 150, and the monitoring server 160 to wirelessly transmit data generated from the components of the system 100 over the network 105. In some instances, the control unit 110 may periodically receive data activity reports from the appliances 120, the sensors 130, the user device 140 and/or the robotic device 150 that include information related to the property, e.g., occupancy data, activity data, movement data, temperature data, among others.

In addition, the control unit 110 can periodically receive sensor data collected by the sensors 130 and the robotic device 150. For example, the control unit 110 can receive input from the user device 140 that indicates that an occupant in the property is presently sick. As discussed below, the control unit 110 can process the received input data to configure the robotic device 150 to perform a sterilization operation of one or more surfaces that are expected to have been used by the occupant during a particular time period. For example, the control unit 110 can instruct the robotic device 150 to sterilize surfaces of a room within the property that is associated with activity data collected for the sick occupant.

The appliances 120 can be home automation devices connected to the network 105 that are configured to exchange electronic communications with other devices of the system 100. The appliances 120 may include, for example, connected kitchen appliances, controllable light sources, safety and security devices, energy management devices, and/or other types of electronic devices capable of exchanging electronic communications over the network 105. In some instances, the appliances 120 may periodically transmit information and/or generated data to the control unit 110 such that the control unit 110 can automatically control the operation of the appliances 120 based on the exchanged communications. For example, the control unit 110 can operate one or more of the appliances 120 based on a fixed schedule specified by the user. In another example, the control unit 110 may enable or disable one or more of the appliances 120 based on received sensor data from the sensors 130.

The sensors 130 may include various types of sensors that are placed within a property. For example, the sensors 130 can include a contact sensor, a motion sensor, a glass break sensor, an occupancy sensor, an activity sensor, or any other type of sensor that is typically included in a monitoring system or security system. The sensors 130 also can also include environmental sensors such as an ambient temperature sensor, a water sensor, a rain sensor, a wind sensor, a light sensor, a smoke detector, a carbon monoxide detector, an air quality sensor, etc. In some instances, the sensors 130 may include a radio-frequency identification (RFID) sensor that identifies a particular article that includes a pre-assigned RFID tag.

The user device 140 can be any type of computing device that is used or associated with a user in association with a property. For instance, the user device 140 can be one or more of a smartphone, wearable device, a tablet computing device, a laptop computing device, or a desktop computing device. The user device 140 can be used to allow a property owner to access, control, and/or configure the system 100 through a monitoring application 142. For example, the monitoring application 142 can allow the property owner to perform various actions, such as transmitting an instruction to the robotic device 150 to perform a sterilization operation, transmitting an instruction to the robotic devices 150 to monitor a certain region of the property 101 for contaminants, or to submit information that indicates a high likelihood of germ or disease transmission in the property, e.g., indicating that a user is presently sick inside the property.

A user can also use monitoring application 142 to control the monitoring operations of system 100. For example, the user can use the monitoring application 142 to turn the appliances 120 on and off, transmit instructions to the sensors 130 to collect and/or store sensor data, or transmit an instruction to the control unit 110 to provide locally stored data to the monitoring server 160. In some instances, the monitoring application 142 enables a user to remote configure the components of the system 100 while he/she is away from the property. For example, if the user is a parent that is at work but has a sick child at home, he/she can use the monitoring application 142 to configure the robotic device 150 to periodically check the property to ensure that germ contamination due to the sick child is limited in the property.

The robotic device 150 may be any type of robot that is capable of moving and taking actions that assist in sterilizing surfaces of a property. For example, the robotic device 150 be a drone that is capable of moving throughout a property based on automated control technology and/or input control provided by a user through an associated device, e.g., a control application through the user device 140 or a separate remote control. In this example, the drone may be able to fly, roll, walk, or otherwise move about the property. The drone may include helicopter type devices, e.g., quad copters, rolling helicopter type devices, e.g., roller copter devices that can fly and also roll along the ground, walls, or ceiling, and land vehicle type devices, e.g., automated cars that drive around a property. In some cases, the robotic device 150 may be a robotic device that is intended for other purposes and merely associated with the system 100 for use in appropriate circumstances. For instance, a robotic vacuum cleaner device may be associated with the monitoring system 100 as the robotic device 150 and may be controlled to act responsive to monitoring system events, e.g., activity data indicating that an occupant is presently sick.

The robotic device 150 can automatically navigate within a property. For instance, the robotic device 150 can include sensors and control processors that guide movement of the robotic device 150 within the property. The robotic device 150 may navigate within the property using one or more cameras, one or more proximity sensors, one or more gyroscopes, one or more accelerometers, one or more magnetometers, a global positioning system (GPS) unit, an altimeter, one or more sonar or laser sensors, and/or any other types of sensors that aid in navigation about a space. The robotic device 150 may also include control processors that process output from the various sensors and control the robotic device 150 to move along a path that reaches the desired destination and avoids obstacles. In this regard, the control processors detect walls or other obstacles in the property and guide movement of the robotic device 150 in a manner that avoids the walls and other obstacles.

The robotic device 150 includes on-board sensors 154 that assist the robotic device 150 to perform various operations in association with the property, such as navigation throughout the property, monitoring for risks of germ or disease transmission, and execution of sterilization operations. For example, the on-board sensors 154 may include data capture and recording devices, such as one or more cameras, one or more motion sensors, one or more microphones, one or more biometric data collection tools, one or more temperature sensors, one or more humidity sensors, one or more air flow sensors, and/or any other types of sensors that may be useful in capturing monitoring data related to the property and users in the property. The one or more biometric data collection tools may be configured to capture biological residues from the air or surfaces of the property that indicate a high likelihood of disease transmission. For example, the one or more biometric data collection tools can enable the robotic device 150 to determine that a liquid sample present on a kitchen countertop carries a harmful bacteria from raw meat.

The on-board sensors 154 can also include output devices. For example, the output devices can include one or more displays, one or more speakers, one or more projectors, and/or any type of output devices that allow the robotic device 150 to communicate information to a nearby user. The one or more projectors may include projectors that project a two-dimensional image onto a surface (e.g., wall, floor, or ceiling) and/or holographic projectors that project three-dimensional holograms into a nearby space.

The robotic device 150 also may include a communication module that enables the robotic device 150 to communicate with the control unit 110, each other, and/or other devices. The communication module may be a wireless communication module that allows the robotic device 150 to communicate wirelessly. For instance, the communication module may be a Wi-Fi module that enables the robotic device 150 to communicate over a local wireless network at the property. The communication module further may be a 900 MHz wireless communication module that enables the robotic device 150 to communicate directly with the control unit 110. Other types of short-range wireless communication protocols, such as Bluetooth, Bluetooth LE, Zwave, Zigbee, etc., may be used to allow the robotic device 150 to communicate with other devices in the property.

The robotic device 150 is associated with one or more charging stations. The charging stations may be located at predefined home base or reference locations in the property. The robotic device 150 may be configured to navigate to the charging stations after completion of tasks needed to be performed for the system 100. For instance, after completion of a sterilization operation or upon instruction by the control unit 110, the robotic device 150 may be configured to automatically fly to and land on one of the charging stations. In this regard, the robotic device 150 may automatically maintain a fully charged battery in a state in which the robotic device 150 are ready for use by the system 100.

The robotic device 150 further may include processor and storage capabilities. The robotic device 150 may include any suitable processing devices that enable the robotic device 150 to operate applications and perform the actions described throughout this disclosure. In addition, the robotic device 150 may include solid state electronic storage that enables the robotic device 150 to store applications, configuration data, collected sensor data, and/or any other type of information available to the robotic device 150.

The robotic device 150 may store spatial data 150A that describes attributes of the property. For instance, the robotic device 150 may store a floorplan and/or a three-dimensional model of the property that enables the robotic device 150 to navigate the property. During initial configuration, the robotic device 150 may receive the data describing attributes of the property, determine a frame of reference to the data, e.g., a home or reference location in the property, and navigate the property based on the frame of reference and the data describing attributes of the property. Further, initial configuration of the robotic device 150 also may include learning of one or more navigation patterns in which a user provides input to control the robotic device 150 to perform a specific navigation action, e.g., fly to an upstairs bedroom and spin around while capturing video and then return to a home charging base. In this regard, the robotic device 150 may learn and store the navigation patterns such that the robotic device 150 may automatically repeat the specific navigation actions upon a later request.

The robotic device 150 may also store and/or maintain a set of sterilization rules 150B. Each rule within the set of sterilization rules 150B can specify one or more triggers or conditions, and one or more actions to be performed by the robotic device 150 in response to satisfaction of the triggers or conditions specified by a rule. For example, a sterilization rule can specify a trigger related to the detection of a liquid contaminant on a monitored surface within the property. In this example, the corresponding action may be to perform sterilization operation that wipes the liquid from the monitored surface and applies UV irradiation to destroy the contaminants on the surface. The set of sterilization rules 150B can specify different types of triggers, conditions, and actions such that the robotic device 150 can perform different actions in response to receiving types of monitored sensor data. For example, the robotic device 150 can apply one sterilization rule corresponding to liquid contaminants to perform a certain type of sterilization operation that removes liquids from a surface but apply another sterilization rule corresponding to aerial contaminants to perform another type of sterilization operation that remove contaminants from the air.

The robotic device 150 can be configured to perform sterilization operations without damaging nearby objects within a property. For example, the robotic device 150 can navigate a property along routes that reduce the likelihood of a collision with objects and/or fixtures. In some implementations, the robotic device 150 can adjust a type of sterilization operation to be performed on a surface based on the presence of an object on the surface and/or attributes associated with the surface. For example, the robotic device 150 can avoid applying UV light onto a highly colored fabric surface. As another example, the robotic device 150 can avoid applying UV light onto a kitchen surface where food to be consumed is placed. In these examples, the robotic device 150 is capable of utilizing object detection and/or recognition techniques to reduce the likelihood of damaging objects or surfaces as a result of performing a sterilization operation.

In some implementations, the robotic device 150 is capable of generating reports after conducting monitoring operations and sterilization operations and providing the generated reports to the user device 140. The reports can identify, for example, the most high risk surfaces based on monitoring the present condition of the property, a predicted likelihood of germ or disease transmission resulting from use of the high risk surfaces, suggested sterilization operations to reduce the risk of germ or disease transmission, among others. In some instances, the reports can also identify sterilization operations that could be automated by the robotic device 150 and other operations that require manual operation to ensure proper sterilization. For example, the application of a liquid cleaning agent on a large flat kitchen countertop is identified as being automated by the robotic device 150 but replacement of a kitchen sink due to rust in the piping system is identified as requiring manual intervention.

In some implementations, the robotic device 150 can use various optimization techniques to manage resource allocation in the execution of monitoring operations or sterilization operations. For example, given a set of finite computational and power restrictions, the robotic device 150 can utilize operational data of the appliances 120 to determine which devices are most frequently used by the user (and therefore more likely to require more frequent monitoring and sterilization). In this example, the robotic device 150 can be configured to prioritize monitoring of surfaces associated with appliances that are more likely to be used in lieu of other devices that are infrequently used by users. In another example, the robotic device 150 can identify the most high risk surfaces based on activity patterns in the property and monitor and sterilize only the most high risk surfaces to conserve resources. For example, if there are two bathrooms in a property and only one is frequently used by users, then the robotic device 150, in this example, prioritizes the monitoring and sterilization of the frequently used bathroom to reduce the risk of germ or disease transmission while conserving resources by limiting the monitoring or sterilizing a bathroom that is not frequently in use.

In some implementations, the robotic device 150 can configure the execution of sterilization operations in a manner that preserves cleaning reagents based on the number of anticipated sterilization operations. For instance, if the robotic device 150 manages 1 L of a cleaning reagent, then the robotic device 150 can allocate a portion of the cleaning agent for each of five sterilization operations based on, for example, the surface area of a surface involved in a sterilization operation, whether the sterilization operation is classified as heavy or light sterilization, or a prioritization associated with a surface to be sterilized by the sterilization operation.

In some implementations, the robotic device 150 can perform sterilization operations to decrease the spread of allergens such as pet dander. For example, if the robotic device 150 determines that an area of a property is used by a pet, then the robotic device 150 can perform operations in relation to the area of the property more frequently to decrease the spread of allergens. In this example, the robotic device 150 can more frequently perform sterilization operations in the area compared to other areas of the robotic device 150 based on determining that the area frequently used by the pet is more likely to increase the spread of allergens than other areas of the property. As another example, the robotic device 150 can adjust the frequency of monitoring based on whether a user in the property is identified as having certain allergies. For example, if an occupant is identified as having a dust allergy, then the robotic device 150 can be configured to identify areas of the property that are likely to accumulate dust, such as the floor underneath furniture, and more frequently perform sterilization operations in the identified areas to reduce the accumulation of dust. In some implementations, the robotic device 150 may perform sterilization operations that include vacuuming pet dander or triggering another robotic device that includes a vacuum to clean the identified area.

The monitoring server 160 can be an electronic device configured to provide monitoring services in association with a property by exchanging electronic communications with the control unit 110, the robotic device 150, and/or the user device 140 over the network 105. For example, the monitoring server 160 can be configured to monitor events, e.g., user input indicating a sick occupant in a property, activity data collected the control unit 110 within the property, sensor data collected by the sensors 130, or sterilization operations performed by the robotic device 150. In these examples, the monitoring server 160 may exchange electronic communications with the network module 112 to receive information regarding events detected by the control unit 110. The monitoring server 160 can also receive information regarding events from the robotic device 150, e.g., data indicating a recently executed sterilization operation within a property.

The monitoring server 160 can store data that is used to enable the robotic device 150 perform sterilization operations in the manner discussed throughout. For example, the monitoring server 160 can store activity data that indicates usage patterns of the property that may be relevant to determining how and when to sterilize surfaces of the property. In another example, the monitoring server 160 can store historical data that indicates prior sterilization operations performed by the robotic device 150 that identifies reoccurring activity patterns that can then be used to automatically, i.e., without receiving any user input, predict when a subsequent sterilization operation should be performed by the robotic device 150.

In some implementations, the robotic device 150 can be configured to apply automated monitoring techniques to improve the quality of sterilization to reduce the likelihood of germ or disease transmission that may be possible using alternative manual techniques. For example, the robotic device 150 can be configured to combine topological surface analysis with activity data monitoring, and spatial information to more accurately identify surfaces that are likely to have contaminants. As discussed below, to accomplish this, the robotic device 150 is capable of processing how a surface has been used, e.g., activity data, in tandem with characteristics of the surface, e.g., image and object recognition data, and the detection of contaminants or other conditions that may increase the likelihood of germ or disease transmission.

Due to the various types of data captured by the robotic device 150 that represent how a property is used by users, the robotic device 150 is capable contextualizing the sterilization process to more accurately differentiate between user activity that is likely to result in germ transmission and user activity that does not. For example, if historical user activity indicates that a user often does not sanitize a certain region after heavy use, then this information can be used to increase the likelihood that, after a user uses the certain region in a similar manner, that the robotic device 150 determines that surfaces in the certain region have an increased risk of germ or disease transmission. As another example, if appliance data indicates that a particular appliance has been used, then activity data can be processed in parallel to determine what type of use has occurred, which the robotic device 150 uses to more accurately predict the likelihood of germ or disease transmission. For instance, a kitchen oven being used to heat a frozen pizza may result in a lower likelihood of germ or disease transmission compared to the kitchen over being used to heat and cook raw meat.

Figure 2:
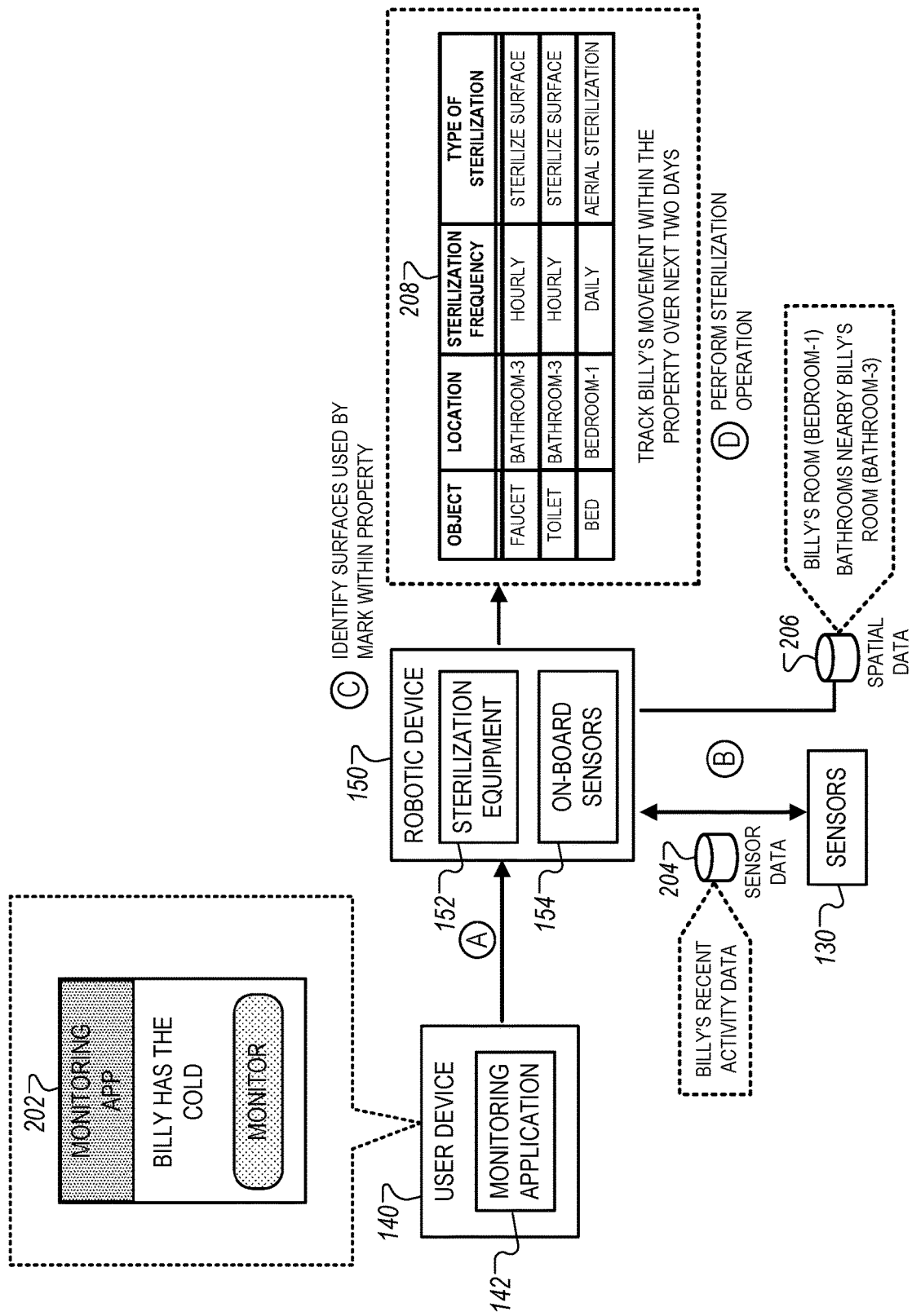
FIG. 2 illustrates an example of a technique for sterilizing regions of a residential property.

FIG. 2 illustrates an example of a technique for sterilizing regions of a residential property. In this example, a parent directs the robotic device 150 to perform a sterilization operation in a residential property based on identifying that a sick child presently resides in the property. The robotic device 150, in this example, monitors and sterilizes certain surfaces of the property that have been used or accessed by the sick child to prevent the transmission of germs/diseases and/or reduce ongoing contaminations of the surfaces to improve the recovery of the sick user.

As shown in FIG. 2, at step (A), a parent initially accesses an interface 202 of the monitoring application 142 through the user device 140. The user can be a parent of a child that is sick with a communicable disease, such as the common cold or flu. The parent provides input on the interface 202 to indicate that her son, Billy, is currently sick. The input provided on the interface 202 results in an instruction being provided to the robotic device 150 to monitor the property for potential germ or disease transmission risks.

At step (B), the robotic device 150 obtains sensor data 204 from the sensors 130 and spatial data 206 of the property in response to receiving the instruction from the user device 140. The sensor data 204 includes Billy's recent activity data, such as rooms occupied, appliances used, doors used, and objects interacted with. The spatial data 206 identifies regions of the property that may be susceptible to germs since they are associated with Billy, such as Billy's bedroom and bathrooms near Billy's room.

At step (C), the robotic device 150 identifies surfaces to be sterilized based processing information in the sensor data 204 and the spatial data 206. For example, as shown in table 208, the robotic device 150 identifies objects "FAUCET," "TOILET," and "BED" as objects that likely to be susceptible to germ contamination since they are most likely to be used by Billy while he is sick. Additionally, the robotic device 150 identifies a frequency to monitor and sterilize each object based on the frequency of usage by other users. For example, objects "FAUCET" and "TOILET" are sterilized hourly because the robotic device 150 determines that these objects are likely to be used by other occupants of the property while the object "BED" is uniquely associated with Billy and unlikely be used by another occupant. The robotic device 150 therefore monitors and sterilizes the object "BED" on a daily basis.

In some implementations, the robotic devices 150 identifies surfaces to be sterilized based on identifying the surfaces that Billy has touched in a period of time, e.g., during the previous day. To identify these surfaces, the robotic device 150 processes sensor data collected by the sensors 130 to determine Billy's activity patterns. For example, the robotic device 150 can follow Billy throughout the day and capture images that identify surfaces that were touched by Billy during the day. In other examples, the robotic device 150 can infer surfaces that were touched by Billy based on processing different types of sensor data collected by the sensors 130. For instance, the robotic device 150 can process data collected by a door sensor indicating that the bathroom has been used during a particular day along with data collected by a presence sensor that indicates only Billy has occupied the property during the particular day. The robotic device 150, in this instance, can determine that Billy has used the bathroom without actual visual confirmation.

The robotic device 150 also identifies the type of sterilization to perform on each object based on the type that of object and Billy's predicted usage. For example, the robotic device 150 determines to perform surface sterilization for objects "FAUCET" and "TOILET" but aerial sterilization for object "BED" since Billy is likely to use the first two objects for short periods of time, but spend large amounts of time in bed. In this example, the robotic device 150 performs surface sterilization to prevent transmission of germs from Billy to other occupants, and performs aerial sterilization to reduce the amount of germs in Billy's room to improve Billy's speed of recovery.

At step (D), the robotic device 150 performs a sterilization operation according to the specifications in the table 208 over the next two days. For example, the robotic device 150 monitors the faucet and toilet on an hourly basis and monitors the bed on a daily basis. Each time the robotic device 150 monitors an object, the on-board sensors collect sensor data that is used to determine if surfaces associated with the monitored object requires sterilization. For instance, if the robotic device 150 detects the presence of saliva in the faucet and the sensor data 204 indicates that Billy was the last occupant to enter the bathroom, then the robotic device 150 may determine that sterilization may be needed, and in response, performs surface sterilization as specified by the table 208.

Figure 3:
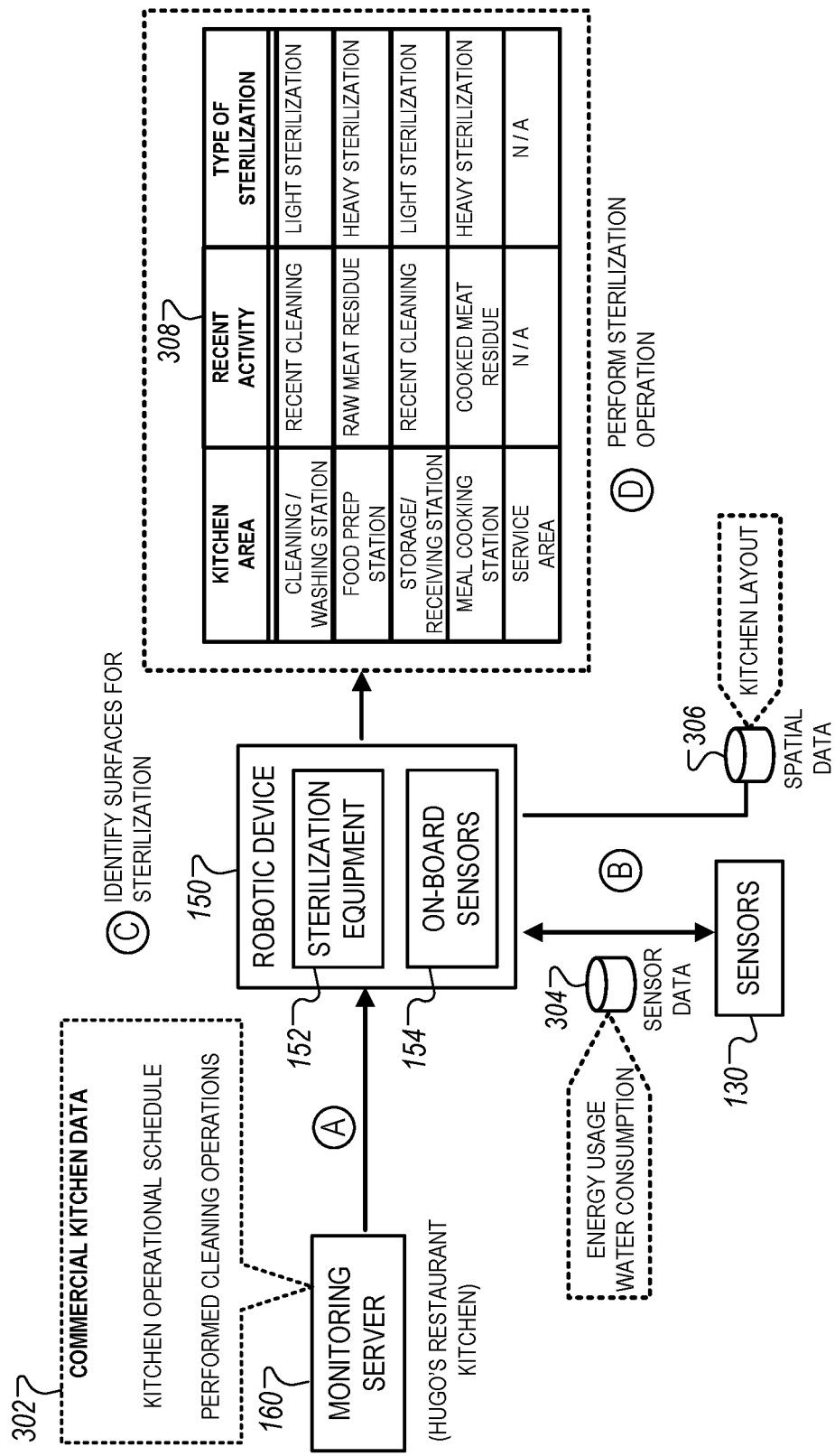
FIG. 3 illustrates an example of a technique for sterilizing regions of a commercial property.

FIG. 3 illustrates an example of a technique for sterilizing regions of a commercial property. In this example, the robotic device 150 is configured to monitor a commercial kitchen with minimal or no minimal intervention so that the sterilization operations performed by the robotic device 150 improve the sterility of the kitchen beyond manual cleaning operations performed by staff members. The robotic device, in this example, is configured to perform monitoring and sterilization operations according to the kitchen's operational schedule so that it operates during a time period when the kitchen is not in use, e.g., after business hours when the kitchen is closed.

As shown in FIG. 3, at step (A), the monitoring server 160 provides kitchen data 302 to the robotic device 150. The kitchen data 302 specifies a kitchen operational schedule, e.g., operating hours for the kitchen, and cleaning operations that have been identified as being performed by maintenance or cleaning staff in the kitchen. For example, the kitchen data 302 can include maintenance log data that is submitted by cleaning staff each time they clean the kitchen. The kitchen data 302 can indicate, for example, types of cleaning products that have been applied to surfaces of the kitchen, time points when staff cleaned the kitchen, or the types of equipment that were used to clean kitchen surfaces.

At step (B), the robotic device 150 obtains sensor data 304 from the sensors 130 and spatial data 306 of the kitchen in response to receiving the kitchen data 302 from the monitoring server 160. The sensor data 304 includes activity data associated with kitchen usage, such as energy consumption, water consumption, or types of meals prepared in the kitchen for a given period of time, e.g., one business day. This information can be used by the robotic device 150 to determine which parts of the kitchen were more frequently used during the time period (which increases the likelihood that it may require further monitoring and sterilization). The spatial data 306 identifies a layout of the kitchen, including appliances, sinks, and countertops, among others. The robotic device 150 uses the spatial data 306 to identify locations of surfaces that might need be sterilized based on the information included in the kitchen data 302.

At step (C), the robotic device 150 identifies surfaces to be sterilized based processing information in the sensor data 304 and the spatial data 306. For example, as shown in table 308, the robotic device 150 identifies different regions of the kitchen, etc., cleaning station, food preparation station, storage/receiving station, meal cooking station, service area, which may need sterilization based on recent activity in each region as indicated in the kitchen data 302 and the sensor data 304.

The robotic device 150 identifies a type of sterilization operation to be performed in each region based on the type of activity recently performed in each region. For example, the robotic device 150 determines that the cleaning/washing station and the storage/receiving station may only need light sterilization since the kitchen data 302 indicates that they have been recently cleaned. Additionally, the robotic device 150 determines that the food preparation station and the meal cooking station may need heavy sterilization because the sensor data 304 indicates that meat residue is detected on surfaces of these regions of these regions of the kitchen.

At step (D), the robotic device 150 performs a sterilization operation according to the specifications in the table 308. For example, the robotic device 150 prioritizes sterilization of the food preparation station and the meal cooking station since these regions of the kitchen are most likely to have contaminates due to meat residue detected on their surfaces. As noted above, the robotic device 150 also performs the sterilization operation at a time that the kitchen is not in use so that the sterilization operation does not impede use of the kitchen.

Figure 4:
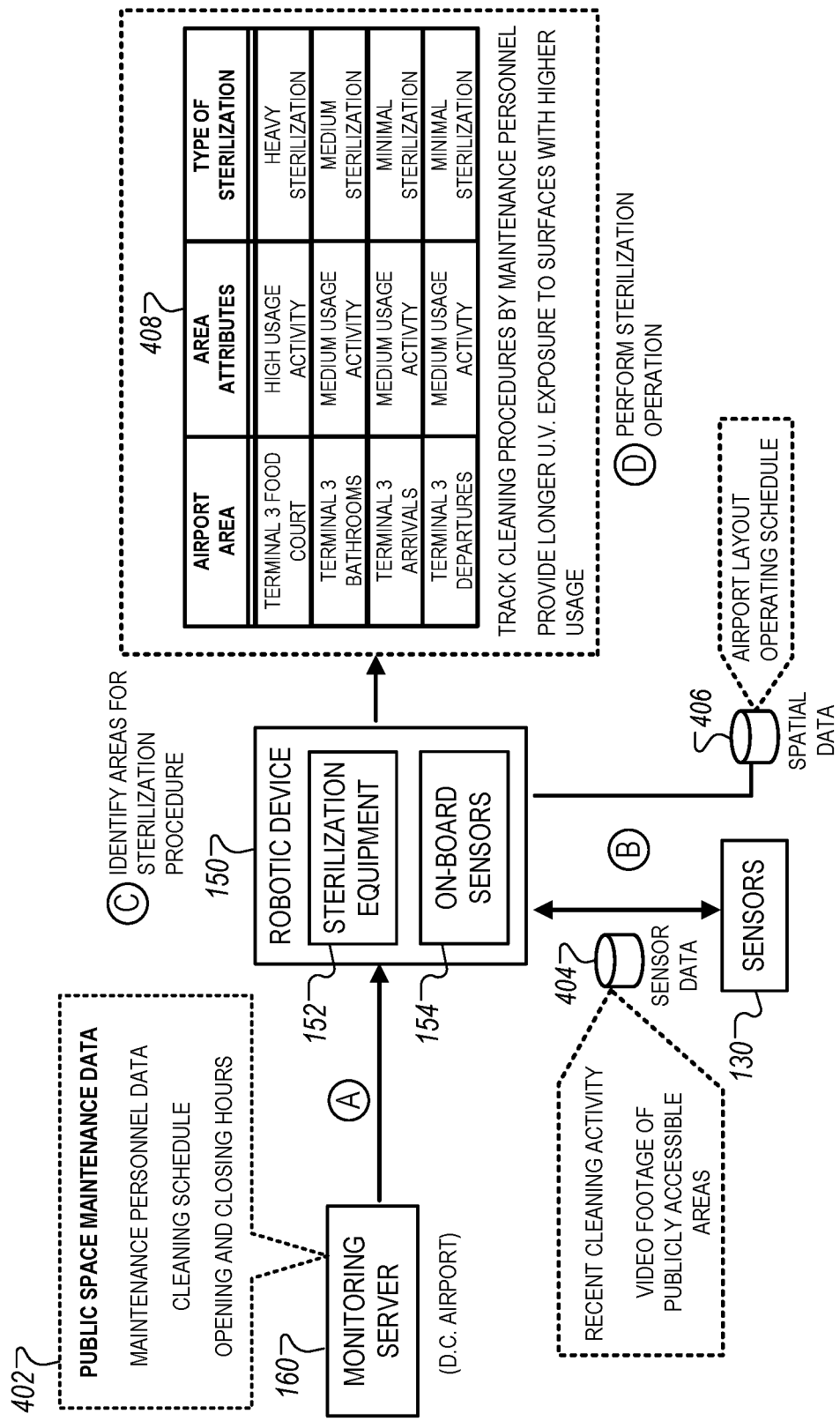
FIG. 4 illustrates an example of a technique for sterilizing regions of a publicly accessible location.

FIG. 4 illustrates an example of a technique for sterilizing regions of a publicly accessible location. In this example, the robotic device 150 is configured to monitor an airport terminal, i.e., a publicly accessible location, in lieu of, or as a supplement to, cleaning operations performed by airport maintenance staff. The robotic device 150, in this example, is configured to monitor the airport terminal to track the deteriorating conditions of surfaces due to periodic use until sterilization may be needed to prevent possible transmission of germs and/or other communicable diseases. Additionally, the robotic device 150 can monitor cleaning operations and public use in tandem to identify the best time periods to perform monitoring and sterilization operations, e.g., during periods of low terminal use.

As shown in FIG. 4, at step (A), the monitoring server 160 provides maintenance data 402 to the robotic device 150. The maintenance data 402 specifies maintenance personnel data, e.g., the number of cleaning personnel assigned to a particular region of the airport terminal, a cleaning schedule, e.g., time points when regions of the airport terminal was last cleaned, and operating hours associated with the terminal, e.g., business hours of food courts, restaurants, or lounges within the airport terminal. The maintenance data 402 can also indicate, for example, types of cleaning products that have been applied to surfaces of the terminal, time points when staff cleaned the regions, or the types of equipment that were used to clean kitchen surfaces.

At step (B), the robotic device 150 obtains sensor data 404 from the sensors 130 and spatial data 406 of the airport terminal in response to receiving the maintenance data 402 from the monitoring server 160. The sensor data 404 includes recent cleaning activity of regions of the terminal, such as when the public bathrooms were last serviced, or when floors of the airport terminal last wiped. The sensor data 404 also includes video footage of publicly accessible regions of the terminal, such as ticketing gates, boarding gates, security access points, among others. The robotic device 150 can apply various analytics to identify activity patterns within the video footage. For example, the robotic device 150 can monitor activity data captured in the video footage to identify regions of the terminal that experience that most frequent activity (and therefore are most likely to need frequent sterilization). As another example, the robotic device 150 can use object and activity recognition to identify regions of the terminal where users perform certain types of activities that are likely to require sterilization, such as eating, cooking, and bathroom use, among others. The spatial data 306 identifies a layout of the airport terminal, including locations of interest, such as ticketing gates, boarding gates, security access points, public rest rooms, food courts, private restaurants, among others. The robotic device 150 uses the spatial data 306 to identify locations of surfaces that might need be sterilized based on the information included in the maintenance data 402 and the sensor data 404.

At step (C), the robotic device 150 identifies surfaces to be sterilized based processing information in the sensor data 404 and the spatial data 406. For example, as shown in table 408, the robotic device 150 identifies different areas of the airport terminal 3, etc., food court, bathrooms, arrivals, departures, that may need sterilization based on recent activity in each region as indicated in the maintenance data 402 and the sensor data 404.

The robotic device 150 identifies area attributes based on processing information included in the sensor data 404, which is then used to classify each identified area of the airport terminal. For example, the robotic device 150 identifies the food court as exhibiting high usage activity based on the sensor data 404 indicating that a larger number of users were captured in video footage of the food court over a specified time period relative to the number of users that were captured in video footage of other areas of the airport terminal, such as the bathrooms, arrivals, and departures, which are identified as have medium usage activity.

The robotic device 150 identifies a type of sterilization operation to perform based on the type of area and the amount of activity detected within an area over a specified time period. For example, the robotic device 150 determines that the food court may need heavy sterilization based on the area being used for food consumption and high usage activity. In contrast, the robotic device 150 determines that the bathrooms may need medium sterilization because, although the area is used for activity that requires cleaning, the medium activity usage makes the bathroom a lower priority for sterilization. Additionally, the robotic device 150 determines that the arrivals and departures areas may need minimal sterilization because the activity within these areas do not involve food consumption and because usage activity is not as high as the food court, where users tend to stay in one location for longer periods of time.

At step (D), the robotic device 150 performs a sterilization operation according to the specifications in the table 408. For example, the robotic device 150 prioritizes sterilization of the food court and bathrooms since these areas of the airport are most likely to have contaminates due to the types of activity performed by users in this area, e.g., food consumption and waste disposal. Additionally, the robotic device 150 can use activity usage information to determine the exposure time for sterilization. For example, the robotic device 150 can provide longer UV exposure to surfaces of the food court compared to surfaces of the bathroom since the table 308 indicates that the food courts are likely to be used more often by users in a given time period.

As noted above, the robotic device 150 can also coordinate execution of the sterilization operations based on the cleaning procedures by maintenance personnel to reduce the likelihood of germ transmission after manual cleaning. For example, the robotic device 150 can use similar techniques as discussed above to monitor cleaning operations by maintenance personnel and identify areas that may require further sterilization after cleaning operations have been completed. In this example, the robotic device 150 can perform a targeted sterilization operation to sterilize only those areas that might be benefited from additional cleaning.

Figure 5:
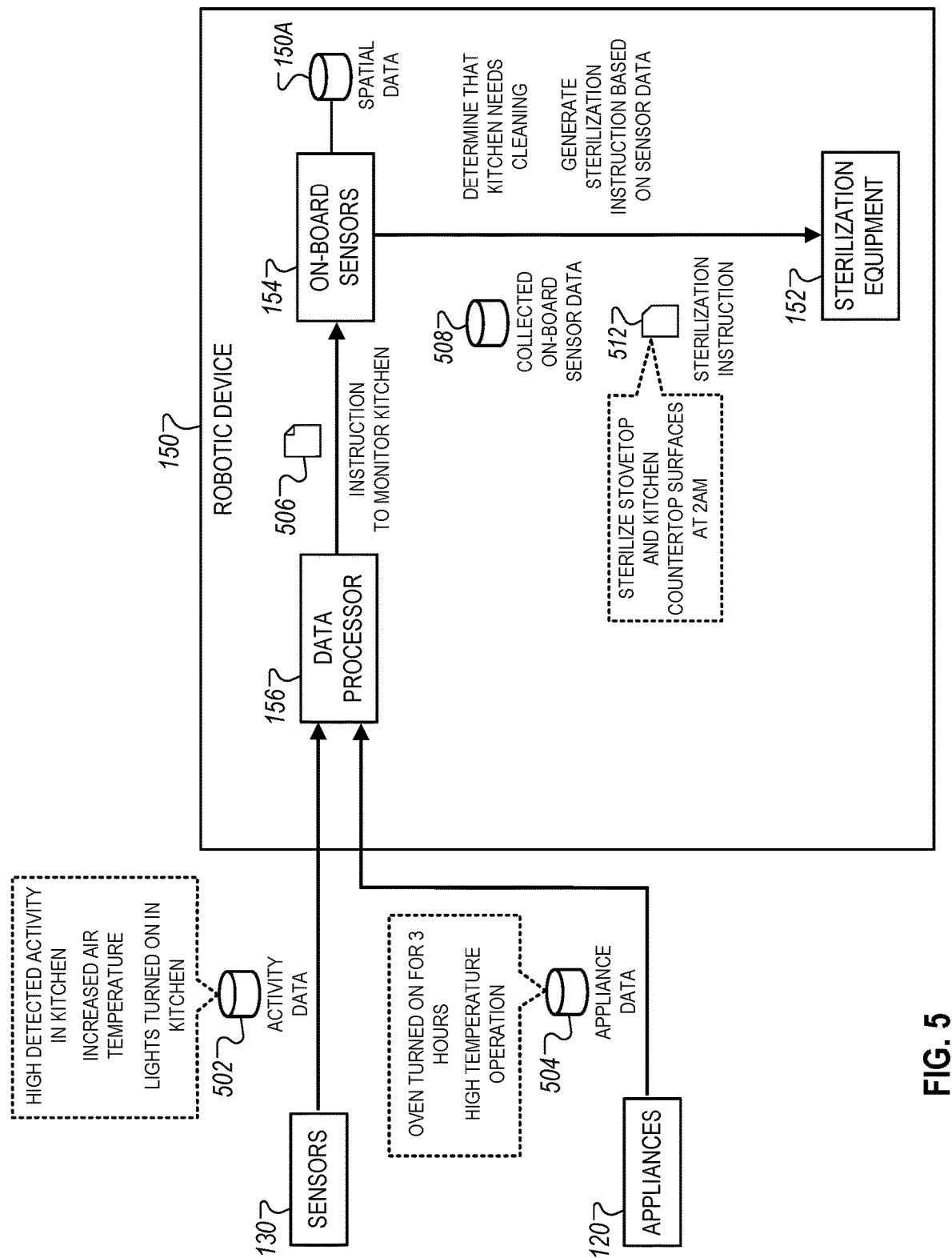
FIG. 5 is a diagram that illustrates an example of a technique for autonomously sterilizing regions of a property.

FIG. 5 is a diagram that illustrates an example of a technique for autonomously sterilizing regions of a property. In this example, the robotic device 150 initiates a monitoring operation, e.g., checking the present condition of the property, and/or a sterilization operation, e.g., applying a sterilization technique on one or more monitored surfaces of the property, with minimal or no human intervention. For instance, instead of being responsive to an instruction provided by a user as depicted in the example of FIG. 2, the robotic device 150 preemptively checks the conditions of a property and initiates a monitoring or sterilization operation based on determining a potential risk of germ or disease transmission.

In the example depicted in FIG. 5, the robotic device 150 includes a data processor 156 that periodically monitors activity data 502 collected by the sensors 130 and appliance data 504 collected by the appliances 120. In the example, the activity data 502 indicates that user activity has recently been detected in the kitchen of a property along with an increase in air temperature and kitchen lights turned on during the same time period. Additionally, the appliance data 504 indicates that the oven has been operational for the last three hours on a high temperature configuration.

The data processor 156 processes information specified in the activity data 502 and the appliance data 504 to determine a likelihood that the kitchen may need to be monitored by the robotic device 150. In some instances, the data processor 156 applies learning-based techniques, e.g., a neural network, to determine a type of activity that has occurred in an associated region of the property based on information specified in the activity data 502 and the appliance data 504. In the example depicted in FIG. 5, the data processor 156 infers that the user used the oven to cook a meal in the kitchen. In this example, the data processor 156 can apply a sterilization rule that instructs the robotic device 150 to monitor a kitchen of a property after the user has been determined to have cooked in the region. The data processor 156 generates an instruction 506 based on applying the sterilization rule and provides the instruction 506 to the on-board sensors 154 of the robotic device 150.

In some implementations, the instruction 506 specifies a location within the property that the robotic device 150 should navigate to in performing a monitoring operation. For instance, in the example depicted in FIG. 5, the data processor 156 processes the activity data 502 and the appliance data 504 to determine that the kitchen of the property is a region of interest. The instruction 506 therefore identifies a region in the spatial data 150A corresponding to the kitchen so that the robotic device 150 can automatically navigate to the kitchen to collect monitoring data in association with the monitoring data. In some other implementations, the identification of regions of interest can be determined based on regions that have a high risk of requiring sterilization. For example, the kitchen or the bathroom of a property can have a higher likelihood of being identified as a region of interest than a living room due to the kitchen and bathroom being identified as high-risk regions.

The on-board sensors 154 perform a monitoring operation as specified by the instruction 506 and based on spatial data 150A that provides spatial information associated with the kitchen of the property. As discussed above, during the monitoring operation, the on-board sensors 154 collect sensor data 508 from surfaces of the kitchen. For example, the on-board sensors 154 can collect images of the kitchen to determine a present cleanliness condition, use liquid sensors to determine the presence of liquid on kitchen countertops or floors, apply biological sensors to determine whether certain biological residues remain on the kitchen countertops or floors, or identify if cleaning reagents have been applied to the kitchen countertops or floors (to determine if the user has attempted to clean the kitchen after cooking). The on-board sensors 154 then process the sensor data 508 to determine that the kitchen needs cleaning.

The on-board sensors 154 generate a sterilization instruction 512 based on processing the sensor data 508 and determining that the kitchen needs cleaning. The sterilization instruction 512 identifies the specific kitchen surfaces that are identified as likely increasing germ or disease transmission, e.g., surfaces that are identified as not being cleaning by the user or having biological residues, such as meat residue, after cooking. The sterilization instruction 512 also identifies a time to perform the sterilization operation so that the robotic device 150 is not obtrusive to users of the property. For example, the sterilization instruction 512 indicates that the robotic device 150 should perform the sterilization operation at or around 2 AM, when the users of the property are expected to be sleeping (and the kitchen is not expected to be used).

In some instances, such as the examples depicted in FIGS. 2-4, the sterilization instruction 512 can also specify the type of sterilization operation to be performed based on information specified in the sensor data 508. For example, the sterilization instruction 512 may specify the amount of sterilization, e.g., light or heavy sterilization, based on how clean the kitchen surfaces are when the robotic device 150 performs the monitoring operation. As another example, the sterilization instruction 512 may specify a type of cleaning agent to apply based on the residues detected in the kitchen. For instance, the sterilization instruction 512 can specify aerial sterilization if odors are detected in the kitchen, and/or surface sterilization if liquid residue not representing water are detected on kitchen countertops. Additionally, the sterilization instruction 512 can specify different cleaning agents to apply based on the user's prior predicted activity in the kitchen. For instance, the sterilization instruction 512 can specify conducting a sterilization operation with a steaming agent if odorous substances were predicted to have been used in cooking, and/or conducting a sterilization operation with a steaming agent with ordinary antibacterial agents if the extent of kitchen use involves microwaving a refrigerated substance.

The robotic device 150 configures the sterilization equipment 152 to perform the sterilization operation in accordance with the sterilization instruction 512. For example, in instances where the robotic device 150 has different types of sterilization options, the robotic device 150 can configure the sterilization equipment 152 to select the appropriate type of cleaning agent and the exposure time while performing the sterilization operation. In other examples, the robotic device 150 has a robotic arm that is attached to an irradiating light source, such as a UV light source. In such examples, the robotic device 150 can configure the robotic arm to apply the irradiating light sources to affected kitchen sources for specified time periods as specified by the sterilization instruction 512.

Figure 6:
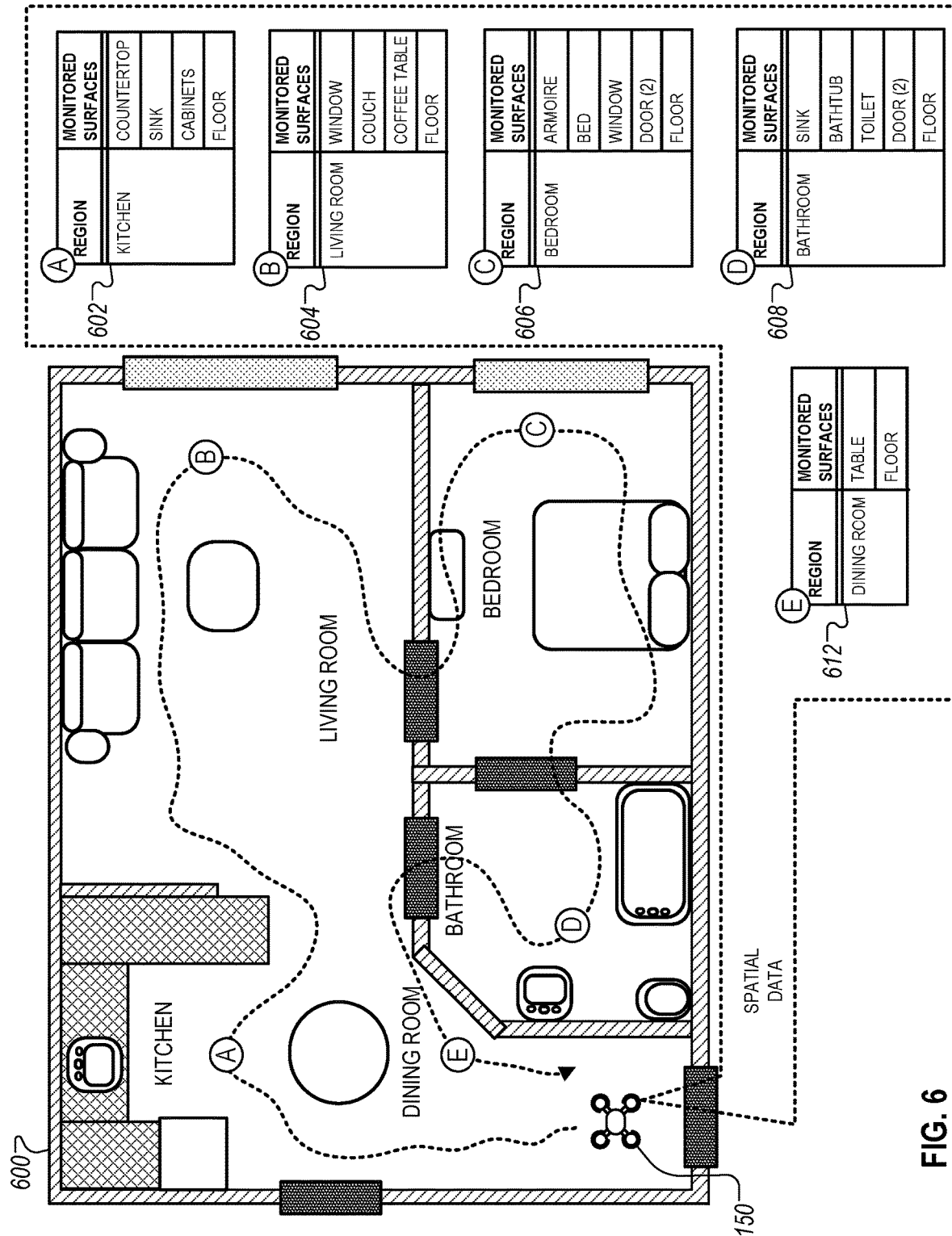
FIG. 6 is a diagram that illustrates an example of a robotic device that is capable of tracking surfaces in a property that may require sterilization.

FIG. 6 is a diagram that illustrates an example of a robotic device that is capable of tracking surfaces in a property that may require sterilization. In this example, the robotic device 150 is a drone that is capable of navigating through an interior environment of a property 600 to track surfaces of interest that may require cleaning or sterilization. For instance, as discussed above, the robotic device 150 may use spatial awareness of the property to identify locations of objects of interests and monitor their present condition to determine whether the monitored object may need sterilization.

In the monitoring operation depicted in FIG. 6, the robotic device 150 navigates through different regions of the property 600 to determine whether the present condition of any monitored surface requires sterilization.

The robotic device 150 performs an initial registration of the interior environment of the property 600 to identify surfaces that may require periodic monitoring for sterilization. The robotic device 150 initially navigates to region "A" corresponding to the kitchen of the property 600. While in this region, the robotic device 150 identifies the countertop, sink, cabinets, and floor as monitored surfaces for the kitchen in table 602. The robotic device 150 then navigates to region "B" corresponding to the living room of the property 600. While in this region, the robotic device 150 identifies the windows, couch, coffee table, and floor as monitored surfaces for the living room in table 605.

The robotic device 150 then navigates to region "C" corresponding to the bedroom of the property 600. While in this region, the robotic device 150 identifies the armoire, bed, windows, doors, and the floor as monitored surfaces for the bedroom in table 606. The robotic device 150 then navigates to region "D" corresponding to the bathroom of the property 600. While in this region, the robotic device 150 identifies the sink, bathtub, toilet, doors, and floor for the bathroom in table 608. The robotic device 150 finally navigates to region "E" corresponding to the dining room of the property 600. While in this region, the robotic device 150 identifies the table and floor for the dining room in table 612.

Once the robotic device 150 has completed the initial registration, the robotic device uses the information specified by tables 602, 604, 606, 608, and 612 to periodically monitor the conditions of the monitored surfaces of each region of the property 600. In some instances, the robotic device 150 can adjust monitoring based on activity data collected in the different regions of the property. For example, if collected activity data indicates that the user of the property 600 frequently uses the kitchen to cook, then the robotic device 150 can monitor the property 600 in a manner that prioritizes the kitchen since the activity patterns increase the likelihood of germ or disease transmission arising out of unclean kitchen surfaces. As another example, if the activity data indicates that the property 600 is unoccupied for a certain period of time when the user is on vacation, then the robotic device 150 can increase the frequency of its monitoring and sterilization operations since the likelihood of germ transmission is heightened as no person is available to manually sanitize the property 600.

Figure 7:
FIG. 7 is a flowchart that illustrates an example of a process for performing a sterilization operation using a robotic device.
Figure 7:
Figure 7:

FIG. 7 illustrates an example of a process 700 for performing a sterilization operation using a robotic device. Briefly, the process 700 can include the operations of obtaining a communication related to sterilization operation associated with a property (710), obtaining sensor data collected by one or more sensors located within the property (720), identifying one or more surfaces within the property for the sterilization operation (730), and performing the sterilization operation (740).

In general, the process 700 is described below in reference to system 100 although other types of property monitoring systems can also be configured to perform the operations of the process 700. For example, a standalone robotic cleaning device, such as a robot vacuum, can be configured to exchange data communications with an existing property monitoring system that collects sensor data to enable the robotic vacuum to perform cleaning operation in a similar manner as described below. In some implementations, the operations of the process 700 are performed by multiple components of the system 100. For example, the control unit 110 can collect sensor data collected by the sensors 130 as described below in step 720, the monitoring server 160 can process the sensor data to identify one or more surfaces within the property for a sterilization operation as described below in step 730, and the robotic device 150 can perform sterilization operation as instructed by the monitoring server 160 as described below in step 740. The descriptions below are in reference to the robotic device 150 as performing the operations of the process 700 for simplicity.

In more detail, the process 700 can include the operation of obtaining a communication related to sterilization operation associated with a property (710). For example, the robotic device 150 can receive a communication that instructs the robotic device 150 to perform a sterilization operation. In some instances, such as the example depicted in FIG. 2, the communication is received as an instruction from the user device 140 based on user input provided through the interface 202. As discussed above, in this example, the communication is received in response a parent indicating that a sick occupant may be located in the property.

In other instances, such as the examples depicted in FIGS. 3 and 4, the communication is received from the monitoring server 160 and includes information that is relevant to determine how and when to perform a sterilization operation. For instance, in the example depicted in FIG. 3, the communication identifies an operational schedule of a commercial kitchen and recently performed cleaning operations, which the robotic device 150 can use to determine which surfaces may need monitoring to determine whether a sterilization operation should be performed.

In some other instances, the communication can be represented as data received from associated devices of the system 100 that periodically monitor activity and condition of the property. In the example depicted in FIG. 5, the robotic device 150 receives activity data 502 and appliance data 504 representing activity and appliance information, respectively, during a specified time period. As discussed above, in such instances, the robotic device 150 can autonomously perform monitoring and sterilization in a manner that requires minimal or no human intervention. For example, the robotic device 150 can determine a risk of germ or disease transmission even if the user is not aware that such a risk exists.

The process 700 can include the operation of obtaining sensor data collected by one or more sensors located within the property (720). For example, the robotic device 150 obtains sensor data collected by the sensors 130 that are located in the property. As discussed above, the sensor data can include various types of information associated with a property, such as presence data of users located in the property, usage data of appliances, temperature data collected by a thermostat, air temperature and humidity data as collected by an HVAC system, or activity or movement data of users within the property. The robotic device 150 can also obtain spatial data that includes a topographical representation of an interior environment of the property. For example, the spatial data can identify a floorplan of the property, indicate locations of monitored surfaces, or represent distinctive spatial features that are used for surface identification and/or navigation through the property.

The process 700 can include the operation of identifying one or more surfaces within the property for the sterilization operation (730). For example, the robotic device 150 can identify surfaces of a property to monitor and sterilize based on processing information in the sensor data obtained in step 720. As shown in the examples depicted in FIGS. 2-3, the robotic device 150 identifies surfaces to sterilize based on determining whether the present conditions of a property and/or activity patterns of users in association with the surfaces indicates a likelihood of germ or disease transmission.

In the example depicted in FIG. 1, the identified surfaces are those surfaces that are located in regions of the property that are predicted to be used by a sick user (and therefore contract germs that may be transmitted to other users that also use the same surfaces). In the example depicted in FIG. 3, the identified surfaces are those surfaces that are identified as being used for activities, such as meat preparation, that often result in biological residue being left on surfaces. In the example depicted in FIG. 4, the identified surfaces are those in areas of an airport terminal that are likely to require cleaning based on the type of activity performed by users as well as the frequency of users interacting with those surfaces.

The process 700 can include the operation of performing the sterilization operation (740). For example, the robotic device 150 performs the sterilization operation on the surfaces identified in step 730. As discussed above in reference to FIG. 1, in some instances, the robotic device 150 determines the appropriate procedure to perform the sterilization operation based on applying a set of sterilization rules 150B that specify a different type of sterilization operation based on triggers associated with a present condition of the property and/or activity information associated with monitored surfaces. For example, the robotic device 150 can perform an aerial sterilization operation that involves spraying an aerosol disinfectant based on detecting the presence of an odor associated with a biological contaminant. As another example, the robotic device 150 can perform a surface sterilization operation that involves applying an irradiated light source on a monitored surface based on determining a high likelihood of bacterial transmission after a sick user has touched the monitored surface.

In performing the sterilization operation, the robotic device 150 can configure and/or adjust the sterilization equipment 152 appropriately based on the type of sterilization performed. For example, in some instances, the robotic device 150 can have a robotic arm attached to cleaning reagents and the robotic arm can be manipulated to apply the cleaning agents to the monitored surface. As another example, the robotic device 150 can adjust the exposure time of an irradiated light source used for sterilization based on an identification of a contaminant that is present on a monitored surface and the likelihood of germ or disease transmission resulting from the presence of the contaminant on the monitored surface.

Figure 8:
FIG. 8 is a flowchart that illustrates an example of a process for determining to perform a sterilization operation based on one or more activity patterns of a user.
Figure 8:
Figure 8:

FIG. 8 is a flowchart that illustrates an example of a process 800 for determining to perform a sterilization operation based on one or more activity patterns of a user. Briefly, the process 800 can include the operations of processing sensor data collected by one or more sensors located in a property (810), identifying one or more activity patterns of a user located within the property (820), determining to perform a sterilization operation (830), and providing an instruction to a robotic device located in the property to perform the sterilization operation (840).

In general, the process 800 is described below in reference to system 100 although other types of property monitoring systems can also be configured to perform the operations of the process 800. For example, as discussed throughout, a standalone robotic cleaning device, such as a robot vacuum, can be configured to exchange data communications with an existing property monitoring system that collects sensor data to enable the robotic vacuum to perform cleaning operation in a similar manner as described below. In some implementations, the operations of the process 800 are performed by multiple components of the system 100. For example, the control unit 110 can collect sensor data collected by the sensors 130 as described below in step 810, the monitoring server 160 can process the sensor data to identify one or more activity patterns of a user as described below in step 820, the monitoring server 160 can then determine to perform a sterilization operation as described below in step 830, and the robotic device 150 can perform sterilization operation as instructed by the monitoring server 160 as described below in step 830. The descriptions below are in reference to the robotic device 150 as performing the operations of the process 800 for simplicity.

As described throughout, an "activity pattern" refers to a trend associated with an activity or behavior that can be used for the purposes of examination or analysis. For instance, an activity pattern of a user can be used to identify a user's activity or behavior within a property over a certain time period (e.g., occupancy in regions of the property, movement throughout the property, actions performed by the user, interactions with a user device while located in the property, etc.).

Activity patterns can be used to make determinations, inferences, and/or predictions relating to circumstances that are likely to increase the likelihood of germ and/or disease transmission (thereby indicating the benefit of performing a sterilization operation). For example, activity patterns indicating that the user is sick can be used to identify surfaces and/or objects that may be contagious for other users located in the property. As another example, activity patterns indicating that the user is exhibiting abnormal behaviors may be used to predict that the user is sick and is likely to be contagious to other users. In some instances, activity patterns may reflect the activity or behavior of multiple users that occupy a certain physical space. For example, an activity pattern of a kitchen can indicate a certain activity and/or behavior that may be detected in the kitchen (e.g., cooking a meal, using an appliance, handling raw meat, etc.).

In more detail, the process 800 can include the operation of processing sensor data collected by one or more sensors located in a property (810). For example, the robotic device 150 can process sensor data collected by the sensors 130. As discussed above, the sensor data can indicate various types of information about a property, such as occupancy information, motion information, temperature information, appliance usage information, user activity information, among others. In some instances, the sensor data is collected by on-board sensors of the robotic device 150, such as a camera, a motion sensor, a microphone, a biometric data collection tool, a temperature sensor, a humidity sensor, an air flow sensor, and/or any other types of sensor that may be useful in capturing monitoring data related to the property and users in the property. The sensor data can be collected on an ongoing basis, or alternatively, periodically at specified intervals (e.g., hourly, daily, weekly, etc.).

The robotic device 150 can process the sensor data in real-time or periodically at specified intervals. For instance, in some implementations, the robotic device 150 can be configured to process the sensor data with minimal delay after receiving the sensor data from the sensors 130 and/or the on-board sensors 154. In other implementations, the robotic device 150 can be configured to process the sensor data collected during specified time periods at regular time points (e.g., processing sensor data collected during each hour on an hourly basis). In some implementations, the robotic device 150 can process certain types of sensor data in real-time, while performing other types of sensor data on a reoccurring basis. For example, motion data detected within a property can be processed in real-time to identify user movement throughout the property, whereas set point temperature data can be processed on an hourly basis to identify changes in ambient temperature within the property.

The process 800 can include the operation of identifying one or more activity patterns of a user located within the property (820). For example, the robotic device 150 can identify one or more activity patterns of a user located within the property. As discussed above, an activity pattern indicates a user's detected movement through the property to identify rooms that are most frequently occupied by the user.

For example, an activity pattern can indicate that the user has occupied a bedroom for six hours during an eight-hour time window when he/she is detected to be inside the property.

In other instances, an activity pattern indicates actions that have been performed by the user (e.g., bathroom usage, appliance usage, etc.) to identify objects or surfaces with which the user has frequently interacted with. For example, an activity pattern can indicate that the user has interacted with a bathroom sink seven times in the last three hours. In some other instances, activity patterns can indicate a user's behavioral patterns based on correlations between different types of sensor data collected for a user. For example, motion data indicating that a user has occupied a bathroom for longer than five minutes and body temperature measured after the user has occupied the bathroom can be used to determine that the user has recently taken a shower.

The process 800 can include the operation of determining to perform a sterilization operation (830). For example, the robotic device 150 can determine to perform a sterilization operation based on the one or more activity patterns identified for the user located within the property. In some instances, the determination to perform a sterilization operation can be made automatically by the robotic device 150 based on determining that a likelihood of germ or disease transmission exceeds a threshold. For example, if the robotic device 150 determines that a user has an infectious disease (e.g., based on an indication from the user), and the determined likelihood of transmission exceed a threshold of thirty percent (e.g., based on a number of surfaces that the user has interacted with after he/she is determined to be infected), then the robotic device 150 can determine to perform a sterilization operation. As other examples, the robotic device 150 can determine a high likelihood of disease transmission if the one or more activity patterns indicate the occurrence of an event that is correlated with a high likelihood of germ or disease transmission (e.g., the user having prepared raw meat in the kitchen, a toilet sensor being activated an unusually high number of times during a certain time period, a user being detected to access prescription medications through his/her mobile device, etc.). In these examples, the robotic device can use machine learning techniques to identify trends and/or patterns that indicate high likelihoods of germ of disease transmission within the sensor data processed in step 810.

In some implementations, the determination to perform a sterilization operation may be performed by a device other than the robotic device 150. For example, in some instances, the control unit 110 and/or the monitoring server 160 can make the determination to perform a sterilization operation based on the one or more identified activity patterns of the user, as discussed above for step 820. In such instances, the control unit 110 or the monitoring server 160 can be capable of using similar data processing and/or data analytics techniques discussed above to determine a high likelihood of disease transmission (e.g., greater than thirty percent likelihood that interacting with a surface will result in disease transmission).

In other instances, the determination to perform a sterilization operation can be made by a user through the user device 140. For example, as shown in FIG. 2, the user can provide an indication through interface 202 that a user is sick, and the indication can then be used to instruct the robotic device 150 to perform a sterilization operation. In these instances, the activity patterns identified in step 820 can be provided for output through the user device 140 to assist the user in determining that a sterilization operation should be performed. For example, the user patterns can be identified in a sterilization report that is accessible through the monitoring application 142 that runs on the user device 140.

In some implementations, the sterilization operation can be determined to be performed based on a likelihood that a user that is not sick will interact with an object that has recently been interacted with by another user that is known to be sick. For example, in monitoring a sick user, the robotic device 150 may track an object that has been touched by the sick user and determine the likelihood that another user within the property will also touch the same object within a threshold time period (e.g., within 5 minutes, 10 minutes, 30 minutes, etc.). An object that is more likely to be touched by multiple users, such as a kitchen door, living room door, living room sofa, can be identified as being more likely to result in germ transmission between the sick user and the other user relative to other objects, such as a bed within a room of the sick user (which is unlikely to be used by the other user). In such implementations, a sterilization operation is determined to be performed if, for instance, two users are determined to have interacted with the object (e.g., collected sensor data indicating two users having touched the same object), or a prediction of a sufficiently high likelihood that a second user will touch an object that has been touched by a sick user within a specified time period (e.g., greater than 60% probability that a user will touch a bathroom faucet within fifteen minutes after the bathroom faucet has been used by the sick user).

The process 800 can include the operation of providing an instruction to a robotic device located in the property to perform the sterilization operation (840). For example, the robotic device 150 can be provided with instructions to perform the sterilization operation. In some instances, as mentioned above in reference to step 830, the robotic device 150 can make the determination to perform a sterilization operation and provide the instruction to a relevant component that executes actions involved in performing the sterilization operation. For example, a processor of the robotic device 150 can provide instructions to locomotion module of the robotic device 150 to navigate to a specified location of the property in which the sterilization operation is to be performed. In this example, the processor can also instruct a robotic arm of the robotic device 150 that carries sterilization equipment to execute the sterilization operation (e.g., applying a disinfectant spray to a surface, applying heat or irradiating a surface, among others).

Alternatively, in some implementations where the determination to perform the sterilization operation is made by a device other than the robotic device 150 (e.g., the control unit 110, the monitoring server 160, the user device 140), the robotic device 150 can be instructed to perform the sterilization operation in step 840. For example, the robotic device 150 can receive one or more commands from the control unit 110 to perform a sterilization operation in a specified manner. In this example, the commands can include, for instance, a location of the property to perform the sterilization operation, an identification of the surfaces to be sterilized, a frequency by which the surface is to be sterilized, the type of sterilization to be performed, and/or the duration of the sterilization operation.

In various implementations, the process 800 can have additional operations that are performed by the components of the system 100. For example, in some implementations, the robotic device 150 can identify an activity pattern that indicates a region within the property that is most frequently occupied by the user. For example, as shown in FIG. 2, the robotic device 150 can track a user's movement throughout the property for two days to identify the rooms that are commonly occupied by the user. In such implementations, the robotic device 150 can also determine to perform the sterilization operation on one or more surfaces associated with the region within the property. For example, in FIG. 2, the sterilization operation can be performed on surfaces associated a faucet and toilet of a bathroom, and surfaces associated with a bed in which the user sleeps. Additionally, in some instances, the instruction to perform the sterilization operation can include an instruction for the robotic device 150 to navigate to a specified region of the property. For example, if the robotic device 150 is stationed in a living room and the sterilization operation is to be performed in a bathroom, then the instructions can assist the robotic device to navigate from the living room to the bathroom.

In some implementations, step 820 includes the operation of identifying an activity pattern that indicates a set of objects that the user has interacted with during a specified time period. For example, as shown in table 208 of FIG. 2, the robotic device 150 can identify objects such as the faucet, toilet, and bed as objects that a user frequently interacts with during a time period in which the user is monitored. In such implementations, step 830 includes the operation of determining to perform the sterilization operation on surfaces associated with the set of objects. For example, as shown in FIG. 2, in performing the sterilization operation, the robotic device 150 is configured to perform surface sterilization on the faucet and toilet, and perform aerial sterilization on the bed.

In some implementations, the process 800 includes additional operations beyond those discussed above. The process 800 can include the operation of receiving an indication that the user is sick during a present time. For example, as shown in FIG. 2, the robotic device 150 can receive an indication from the user device 140 that a user is presently sick. In this example, the user provides input through the interface 202, which results in the determination that a sterilization operation is likely to be performed. In such implementations, step 810 includes the operation of processing a subset of the sensor data that indicates activity data of the user during a specified time period that includes the present time. For example, as shown in FIG. 2, the robotic device 150 can identify a subset of the sensor data 204 collected by the sensors 130 that indicates recent activity data for a user. Additionally, step 820 can include the operation of identifying an activity pattern that indicates a set of objects that the user has interacted with during the specified time period. For example, as shown in FIG. 2, the robotic device 150 can identify objects that the user has interacted with (e.g., faucet, toilet, bed) over a two day time period while being monitored. Moreover, in such implementations, step 830 includes the operation of determining to perform the sterilization operation on surfaces associated with the set of objects. For example, referring again to FIG. 2, the robotic device 150 can sterilize surfaces associated with the faucet and toilet as identified in table 208.

In some implementations, step 830 includes the operation of accessing a set of sterilization rules that each specifies a different condition associated with a high likelihood of disease transmission. For example, as shown in FIG. 3, the robotic device 150 can access the table 308, which identifies types of recent activities that are predetermined to have high likelihoods of disease transmission. As shown in table 308, examples of such conditions include raw meat residue being detected on a surface or cooked meat residue being detected on a surface. Other examples of conditions associated with high likelihoods of disease transmission can include a high detected usage activity of a certain object in a public place, as shown in table 408 of FIG. 4. In such implementations, step 830 can additionally include the operation of determining that the one or more activity patterns of the user satisfies a condition specified by at least one sterilization rule included in the set of sterilization rules. For example, in the example depicted in FIG. 3, if the activity data of the user indicates that he/she has recently cooked a meal and raw meat residue is detected on a kitchen top surface, then the robotic device 150 can determine that a sterilization rule corresponding to the raw meat residue, as identified in table 308, has been satisfied.

In some implementations, step 840 includes the operation of determining a sterilization frequency for the sterilization operation. For example, the robotic device 150 can use the activity patterns identified in step 820 to determine whether the sterilization operation should be periodically performed, and if so, the frequency by which the sterilization operation should be periodically performed. As shown in FIG. 2, the robotic device 150 determines to perform sterilization operations for the bathroom faucets and toilets on an hourly basis and perform a sterilization operation for the bed on a daily basis. In this example, the difference in sterilization frequency may be attributed to bathroom objects having a higher likelihood of disease transmission and/or a greater frequency of use within a given time period. Additionally, step 840 can also include determining a type of sterilization to perform when performing the sterilization operation. For example, the robotic device 150 can determine, for instance, whether to perform surface sterilization or aerial sterilization (as shown in table 208 in FIG. 2), the extensiveness of sterilization to be performed (e.g., light, heavy, as shown in table 308 in FIG. 3), or the duration of performing the sterilization (i.e., exposure time for a sterilization agent that is applied to a surface), as shown in table 408 in FIG. 4.

The described systems, methods, and techniques may be implemented in digital electronic circuitry, computer hardware, firmware, software, or in combinations of these elements. Apparatus implementing these techniques may include appropriate input and output devices, a computer processor, and a computer program product tangibly embodied in a machine-readable storage device for execution by a programmable processor. A process implementing these techniques may be performed by a programmable processor executing a program of instructions to perform desired functions by operating on input data and generating appropriate output. The techniques may be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices;

magnetic disks such as internal hard disks and removable disks; magneto-optical disks; and Compact Disc Read-Only Memory (CD-ROM). Any of the foregoing may be supplemented by, or incorporated in, specially designed application-specific integrated circuits (ASICs).

It will be understood that various modifications may be made. For example, other useful implementations could be achieved if steps of the disclosed techniques were performed in a different order and/or if components in the disclosed systems were combined in a different manner and/or replaced or supplemented by other components. Accordingly, other implementations are within the scope of the disclosure.

The invention claimed is:

1. A method performed by one or more computers, the method comprising:
   identifying a set of surfaces that a person interacted with over a time period;
   predicting, based at least on interactions between the person and the set of surfaces over the time period, that one or more surfaces, from among the set of surfaces, are likely to need sterilization, the predicting comprising:
      determining, from a plurality of interaction types, a type of interaction between the person and the one or more surfaces over the time period;
      determining that the type of interaction is likely to increase transmissibility of a communicable disease or a germ within a property; and
      in response to determining that the type of interaction is likely to increase transmissibility of the communicable disease within the property, predicting that the one or more surfaces are likely to need sterilization;
   determining to perform a sterilization operation based on predicting that the one or more surfaces are likely to need sterilization; and
   configuring a robotic device to perform the sterilization operation.

2. The method of claim 1, wherein predicting that the one or more surfaces are likely to need sterilization comprises:
   determining frequencies with which the person interacted with the one or more surfaces over the time period;
   determining that the person mostly interacted with the one or more surfaces from among the set of surfaces over the time period using the determined frequencies; and
   in response to determining that the person has mostly interacted with the one or more surfaces from among the set of surfaces over the time period, predicting that the one or more surfaces are likely to need sterilization.

3. The method of claim 1, wherein the type of interaction between the person and the one or more surfaces over the time period comprises an activity that is likely to increase a likelihood of a bacterial infection on the one or more surfaces.

4. The method of claim 1, wherein determining to perform the sterilization operation comprises:
   accessing a set of sterilization rules that each specifies a different condition associated with a need for sterilization;
   determining that the interactions between the person and the set of surfaces over the time period satisfy a condition specified by at least one sterilization rule included in the set of sterilization rules; and
   in response to determining that the interactions between the person and the set of surfaces over the time period satisfy the condition specified by the at least one sterilization rule included in the set of sterilization rules, determining to perform the sterilization operation.

5. The method of claim 1, wherein determining to perform the sterilization operation comprises:
   determining a sterilization frequency for the sterilization operation; and
   determining a type of sterilization to perform when performing the sterilization operation.

6. The method of claim 1, wherein predicting that the one or more surfaces are likely to need sterilization comprises predicting that the one or more surfaces are likely to increase transmissibility of a communicable disease, a germ, or a biological residue within a property.

7. The method of claim 1, comprising:
   accessing a plurality of sterilization rules that each indicate a condition and a corresponding sterilization procedure; and
   determining that a type of the interaction between the person and a surface from the one or more surfaces satisfy the condition for a first sterilization rule from the plurality of sterilization rules with a first sterilization procedure that is a different procedure than a second sterilization procedure for a second, different sterilization rule, wherein:
   configuring the robotic device comprises configuring the robotic device to perform the first sterilization procedure.

8. The method of claim 7, wherein:
   at least some sterilization rules in the plurality of sterilization rules have a corresponding risk type, at least some of the risk types being different; and
   determining that one or more attributes for the interaction between the person and the second surface satisfy the condition comprises determining that the one or more attributes for the interaction between the person and the second surface satisfy the condition for the first sterilization rule with a first risk type.

9. The method of claim 7, wherein:
   configuring the robotic device comprises configuring, using data for the first sterilization procedure, one or more settings of the robotic device.

10. A system comprising:
    one or more computing devices; and
    one or more storage devices storing instructions that cause the one or more computing devices to perform operations comprising:
       identifying a set of surfaces that a person interacted with over a time period;
       predicting, based at least on interactions between the person and the set of surfaces over the time period, that one or more surfaces, from among the set of surfaces, are likely to need sterilization, the predicting comprising:
          determining, from a plurality of interaction types, a type of interaction between the person and the one or more surfaces over the time period;
          determining that the type of interaction is likely to increase transmissibility of a communicable disease or a germ within a property; and
          in response to determining that the type of interaction is likely to increase transmissibility of the communicable disease within the property, predicting that the one or more surfaces are likely to need sterilization;

determining to perform a sterilization operation based on predicting that the one or more surfaces are likely to need sterilization; and configuring a robotic device to perform the sterilization operation.

11. The system of claim 10, wherein predicting that the one or more surfaces are likely to need sterilization comprises:

determining frequencies with which the person interacted with the one or more surfaces over the time period;

determining that the person mostly interacted with the one or more surfaces from among the set of surfaces over the time period using the determined frequencies; and in response to determining that the person has mostly interacted with the one or more surfaces from among the set of surfaces over the time period, predicting that the one or more surfaces are likely to need sterilization.

12. The system of claim 10, wherein the type of interaction between the person and the one or more surfaces over the time period comprises an activity that is likely to increase a likelihood of a bacterial infection on the one or more surfaces.

13. The system of claim 10, wherein determining to perform the sterilization operation comprises:

accessing a set of sterilization rules that each specifies a different condition associated with a need for sterilization;

determining that the interactions between the person and the set of surfaces over the time period satisfy a condition specified by at least one sterilization rule included in the set of sterilization rules; and in response to determining that the interactions between the person and the set of surfaces over the time period satisfy the condition specified by the at least one sterilization rule included in the set of sterilization rules, determining to perform the sterilization operation.

14. The system of claim 10, the operations comprising:

accessing a plurality of sterilization rules that each indicate a condition and a corresponding sterilization procedure; and determining that a type of the interaction between the person and a surface from the one or more surfaces satisfy the condition for a first sterilization rule from the plurality of sterilization rules with a first sterilization procedure that is a different procedure than a second sterilization procedure for a second, different sterilization rule, wherein:

configuring the robotic device comprises configuring the robotic device to perform the first sterilization procedure.

15. The system of claim 14, wherein:

configuring the robotic device comprises configuring, using data for the first sterilization procedure, one or more settings of the robotic device.

16. At least one non-transitory computer-readable storage media storing instructions that cause one or more processors to perform operations comprising:

identifying a set of surfaces that a person interacted with over a time period;

predicting, based at least on interactions between the person and the set of surfaces over the time period, that one or more surfaces, from among the set of surfaces, are likely to need sterilization, the predicting comprising:

determining, from a plurality of interaction types, a type of interaction between the person and the one or more surfaces over the time period;

determining that the type of interaction is likely to increase transmissibility of a communicable disease or a germ within a property; and in response to determining that the type of interaction is likely to increase transmissibility of the communicable disease within the property. predicting that the one or more surfaces are likely to need sterilization;

determining to perform a sterilization operation based on predicting that the one or more surfaces are likely to need sterilization; and configuring a robotic device to perform the sterilization operation.

17. The storage media of claim 16, wherein predicting that the one or more surfaces are likely to need sterilization comprises:

determining frequencies with which the person interacted with the one or more surfaces over the time period;

determining that the person mostly interacted with the one or more surfaces from among the set of surfaces over the time period using the determined frequencies; and in response to determining that the person has mostly interacted with the one or more surfaces from among the set of surfaces over the time period, predicting that the one or more surfaces are likely to need sterilization.

18. The storage media of claim 16, wherein the type of interaction between the person and the one or more surfaces over the time period comprises an activity that is likely to increase a likelihood of a bacterial infection on the one or more surfaces.

19. The storage media of claim 16, wherein determining to perform the sterilization operation comprises:

accessing a set of sterilization rules that each specifies a different condition associated with a need for sterilization;

determining that the interactions between the person and the set of surfaces over the time period satisfy a condition specified by at least one sterilization rule included in the set of sterilization rules; and in response to determining that the interactions between the person and the set of surfaces over the time period satisfy the condition specified by the at least one sterilization rule included in the set of sterilization rules, determining to perform the sterilization operation.

20. The storage media of claim 16, the operations comprising:

accessing a plurality of sterilization rules that each indicate a condition and a corresponding sterilization procedure; and determining that a type of the interaction between the person and a surface from the one or more surfaces satisfy the condition for a first sterilization rule from the plurality of sterilization rules with a first sterilization procedure that is a different procedure than a second sterilization procedure for a second, different sterilization rule, wherein:

configuring the robotic device comprises configuring the robotic device to perform the first sterilization procedure.

* * * * *

UNITED STATES PATENT AND TRADEMARK OFFICE
CERTIFICATE OF CORRECTION

| | | |
|---|---|---|
| PATENT NO. | : 12,046,373 B2 | Page 1 of 1 |
| APPLICATION NO. | : 17/863772 | |
| DATED | : July 23, 2024 | |
| INVENTOR(S) | : Matthew Daniel Correnti | |

It is certified that error appears in the above-identified patent and that said Letters Patent is hereby corrected as shown below:

On the Title Page

Item (56), Column 2 (Other Publications), Line 2, delete "viruses, """ and insert -- viruses," --.

In the Claims

In Claim 16, Column 28, Line 9, delete "property." and insert -- property, --.

Signed and Sealed this
Third Day of September, 2024

*Katherine Kelly Vidal*

Katherine Kelly Vidal
*Director of the United States Patent and Trademark Office*